(12) United States Patent
Sassenfeld et al.

(10) Patent No.: US 7,544,784 B2
(45) Date of Patent: *Jun. 9, 2009

(54) INCREASED RECOVERY OF ACTIVE PROTEINS

(75) Inventors: Helmut M. Sassenfeld, Bainbridge Island, WA (US); Richard L. Remmele, Jr., Lynnwood, WA (US); Rebecca E. McCoy, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/603,544

(22) Filed: Nov. 22, 2006

(65) Prior Publication Data

US 2007/0270577 A1    Nov. 22, 2007

Related U.S. Application Data

(62) Division of application No. 10/080,471, filed on Feb. 22, 2002, now Pat. No. 7,157,557.

(60) Provisional application No. 60/271,033, filed on Feb. 23, 2001.

(51) Int. Cl.
*C07K 1/14* (2006.01)
*C07K 1/16* (2006.01)
*C07K 1/30* (2006.01)

(52) U.S. Cl. .............. 530/412; 530/417; 530/418; 530/419

(58) Field of Classification Search .............. None
See application file for complete search history.

(56) References Cited

U.S. PATENT DOCUMENTS

| 4,766,205 | A | 8/1988 | Ghosh-Dastidar |
| 4,970,067 | A * | 11/1990 | Panandiker et al. ...... 424/70.51 |
| 5,447,851 | A | 9/1995 | Beutler et al. |
| 5,453,363 | A | 9/1995 | Rudolph et al. |
| 5,593,865 | A | 1/1997 | Rudolph et al. |
| 5,661,001 | A | 8/1997 | Grossenbacher et al. |
| 5,874,060 | A * | 2/1999 | Armour et al. ............. 424/1.49 |
| 5,879,673 | A | 3/1999 | Thomas |
| 7,157,557 | B2 * | 1/2007 | Sassenfeld et al. .......... 530/350 |
| 2003/0099934 | A1 | 5/2003 | Boudet et al. |

FOREIGN PATENT DOCUMENTS

| EP | 0 293 785 A2 | 5/1988 |
| EP | 0 293 785 | 12/1988 |
| EP | 0 553 494 A1 | 12/1992 |
| EP | 0 433 225 B1 | 4/1999 |
| WO | WO 95/32216 | 11/1995 |
| WO | WO 96/03141 A1 | 2/1996 |
| WO | WO 01/34638 A1 | 5/2001 |
| WO | WO 01/49720 A2 | 7/2001 |

OTHER PUBLICATIONS

U.S. Appl. No. 11/255,528, filed Oct. 21, 2005, Dillon et al.
Creighton, "Disulphide Bonds and Protein Stability," *BioEssays* 8(2):57-63, 1988.
Flamand et al., "Purification and Renaturation of Japanese Encephalitis Virus Nonstructural Glycoprotein NS1 Overproduced by Insect Cells," *Protein Expression and Purification* 6:519-527, 1995.
International Search Report, PCT/US02/05645, mailed Jun. 17, 2003.
The Cytokine Fact Book, Second Edition, Academic Press, 2001, pp. 476-478.
Merli et al., Analytical Biochemistry, Sep. 1, 1995, vol. 320, No. 1, pp. 85-91.

* cited by examiner

*Primary Examiner*—Prema Mertz
(74) *Attorney, Agent, or Firm*—Kathleen Fowler

(57) ABSTRACT

The invention provides methods of increasing yields of desired conformation of proteins. In particular embodiments, the invention includes contacting preparations of a recombinant protein with a reduction/oxidation coupling reagent for a time sufficient to increase the relative proportion of a desired configurational isomer.

35 Claims, 7 Drawing Sheets

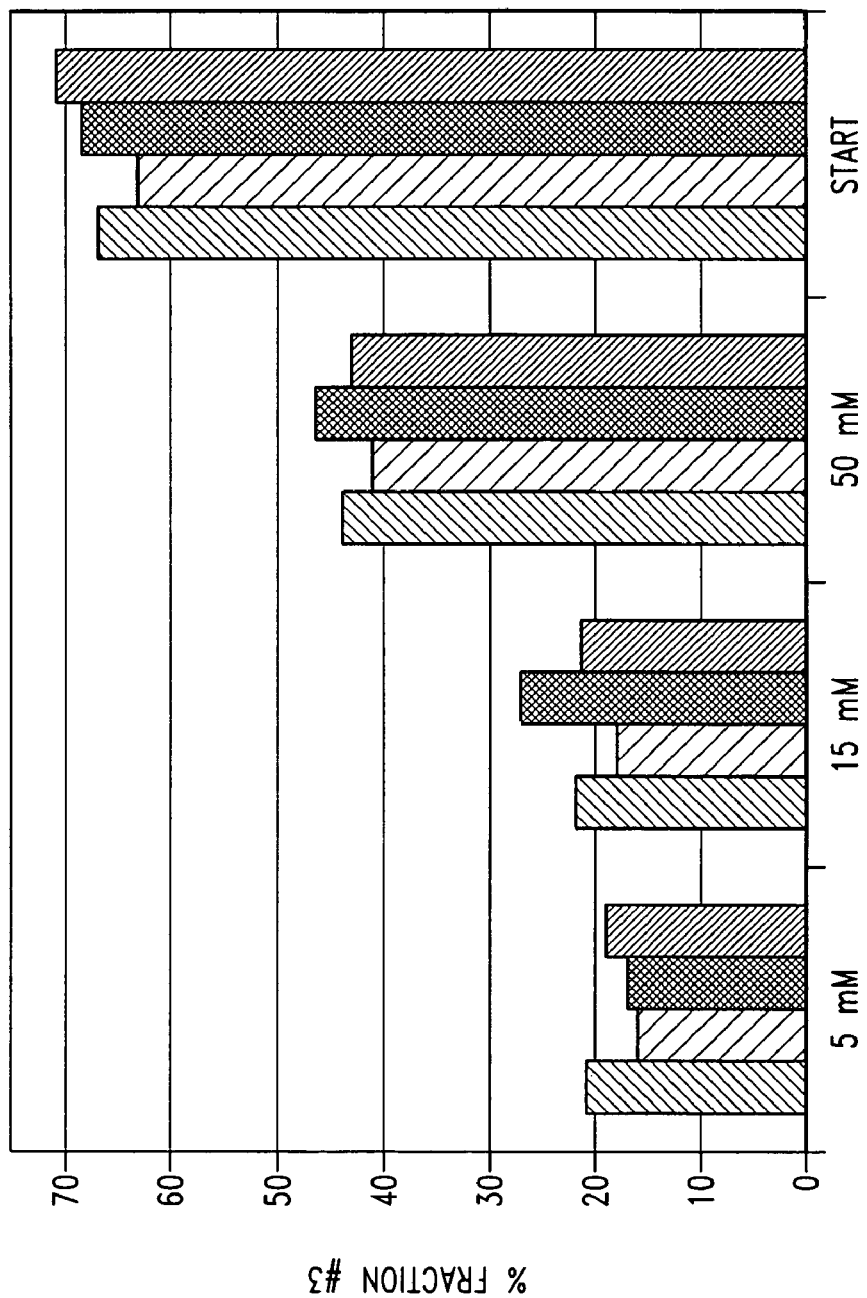

INCREASED RECOVERY OF ACTIVE PROTEINS

This application is a divisional of application Ser. No. 10/080,471, filed Feb. 22, 2002, now U.S. Pat. No. 7,157,557, which claims the benefit of provisional U.S. application 60/271,033, filed Feb. 23, 2001, the disclosure of which is incorporated by reference in its entirety.

FIELD OF THE INVENTION

The invention is in the field of treatment and purification of proteins.

BACKGROUND

High levels of expression of many proteins of eukaryotic origin have been achieved in prokaryotic expression hosts. Such eukaryotic proteins often misfold and accumulate as insoluble inclusion bodies in the prokaryotic host. In order to obtain biologically active protein, the proteins trapped in inclusion bodies had to be unfolded and refolded under harsh conditions including chaotropic agents and reducing thiols.

Expression of proteins of eukaryotic origin in eukaryotic hosts avoided these problems. Provided that the expression vector was properly designed (e.g., with secretory signal peptides, etc.), eukaryotic cell lines tend to correctly process and secrete extracellular eukaryotic proteins as soluble products.

However, as expression systems and vectors have been improved to maximize levels of expression from eukaryotic hosts, not all of the recombinant protein expressed and secreted from these hosts is in the desired, most active conformation. The invention is designed to overcome such expression problems, and maximize yields of biologically active protein.

SUMMARY OF THE INVENTION

The invention is based, in part, on the discovery that not all of the preparation of recombinant protein that is expressed by eukaryotic host cells is folded into a native tertiary conformation. In addition, it has been found that regions or domains of recombinant proteins may be properly folded, while other regions or domains may have undesired conformations. Accordingly, in one aspect, the invention provides a method of contacting a preparation of the recombinant protein that contains a mixture of at least two isomers of the recombinant protein to a reduction/oxidation coupling reagent for a time sufficient to increase the relative proportion of the desired conformational isomer and determining the relative proportion of the desired conformational isomer in the mixture. In another aspect, the invention entails contacting a preparation of a recombinant protein that has been produced by mammalian cells with a reduction/oxidation coupling reagent, at a pH of about 7 to about 11, and isolating a fraction of the preparation of the recombinant protein with a desired conformation. Preferred recombinant proteins are glycosylated recombinant proteins such as, e.g., those produced by eukaryotic cells. The invention also relates to methods of formulating the resulting preparations into a sterile unit dose form, and compositions produced by the methods of the invention.

BRIEF DESCRIPTION OF THE FIGURES

FIG. 2. Circular Dichroism Analysis of Fractions #2 and #3. Near-UV Circular Dichroism measurements expressed in terms of mean residue ellipticity are shown in FIG. 2.

FIG. 3. Molecular Weight Determination Using On-line size exclusion chromatography (SEC), ultraviolet (UV), light scattering (LS), and refractive index (RI) detection in series (On-line SEC/UV/LS/RI).

FIG. 4. Differential Scanning Calorimetry Analysis of Fractions #2 and #3.

FIG. 7. Effect of Cysteine Concentration on Proportion of Fraction #3. Protein samples from four different lots were treated with various concentrations of cysteine (0-50 mM) and the resulting level of Fraction #3 was assessed by HIC.

FIG. 8. Effect of Temperature on Disulfide Exchange. Protein fractions were treated at room temperature or 4 degrees C. in the presence or absence of copper for various times.

DETAILED DESCRIPTION OF THE INVENTION

Figure 1:
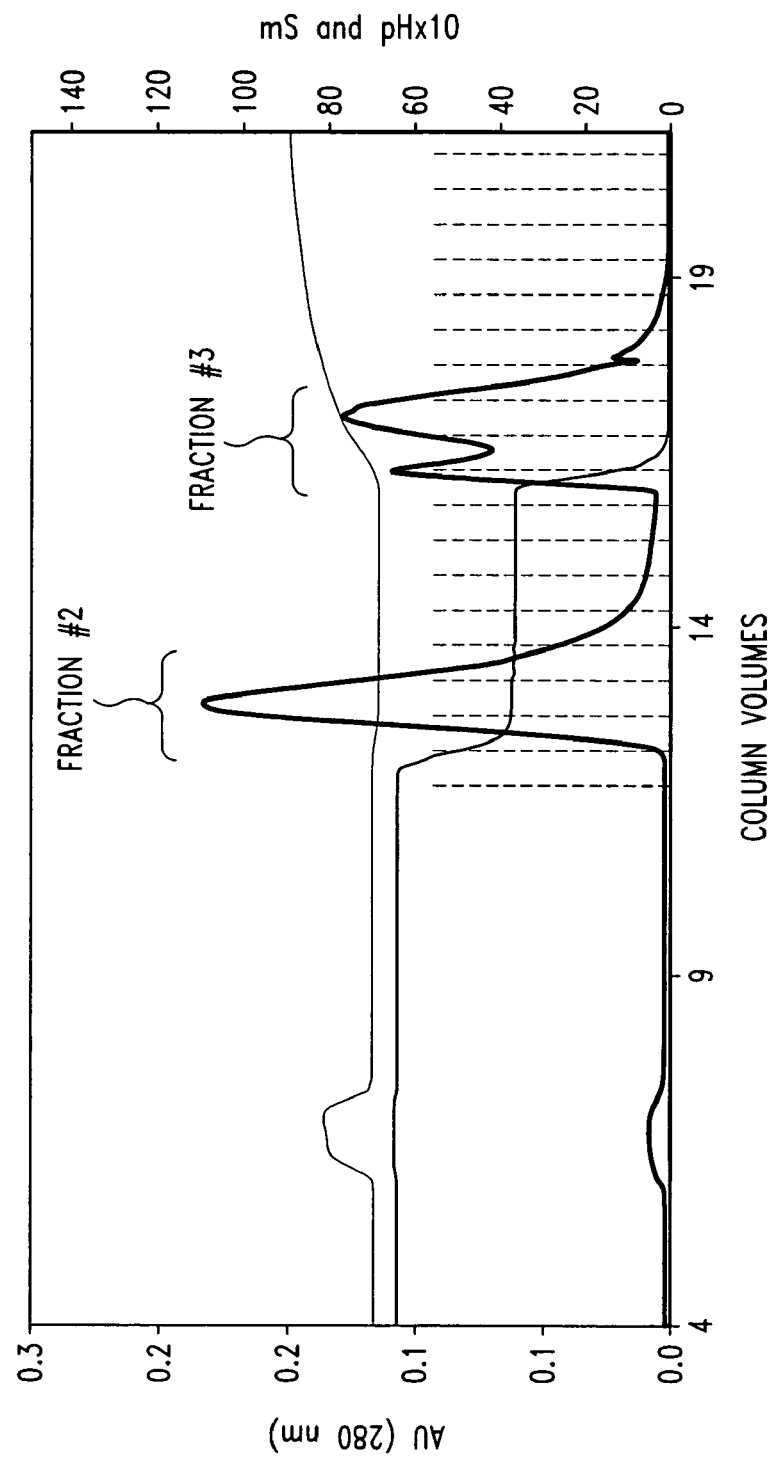
FIG. 1. Hydrophobic interaction chromatography (HIC) of TNFR:Fc. This preparation of TNFR:Fc elutes during HIC as three distinct peaks collected into Fraction #2 and Fraction #3, as indicated.

The invention provides methods of increasing the recovery of active recombinant proteins. In particular, the invention involves promoting a desired conformation of a protein in preparations of a recombinant protein. Significantly, the invention provides gentle methods of altering protein structure without necessitating the use of harsh chaotrope treatments (such as, for example, strong denaturants such as SDS, guanidium hydrochloride or urea). Using the methods of the invention on preparations of recombinant protein results in a higher percentage, or higher relative fraction, of the recombinant protein in the preparation with a desired conformation. A desired conformation for a recombinant protein is the three-dimensional structure of a protein that most closely resembles, and/or duplicates the function of, the naturally occurring domain of that protein. Such gentle methods are particularly advantageous when the recombinant protein is intended to be used in vivo as a drug or biologic.

Generally, when the recombinant protein contains a domain of a receptor protein, the desired conformation will have a higher binding affinity (and, consequently, a lower dissociation constant) for a cognate ligand of the receptor. For example, the desired conformation of a TNF-binding molecule will have a higher binding affinity and a lower dissociation constant for TNF (e.g., TNF-alpha).

In addition, the desired conformation of a recombinant protein is preferably more thermostable than an undesired conformation (when measured in the same solution environment). Thermostability can be measured in any of a number of ways such as, for example, the melting temperature transition (Tm). The desired conformation of a recombinant protein may or may not have a different arrangement of disulfide bonds, although preferably the conformation contains native disulfide bonds. The desired conformation of a recombinant protein may have other tertiary structure characteristics. For example, a desired conformation may be a monomer, dimer, trimer, tetramer, or some other higher order form of the protein. For the purposes of the invention, the "conformation" of a protein is its three-dimensional structure. Two different structures of a polypeptide with the same primary amino acid sequence are "conformers" of each other when they have different conformations corresponding to energy minima, and they differ from each other only in the way their atoms are oriented in space. Conformers can be interconverting (referring to the rotational freedom around bonds to the exclusion of breaking bonds). Two different structures of a polypeptide with the same primary amino acid sequence are "configurational isomers" when they have different conformations corresponding to energy minima, they differ from each other in the way their atoms are oriented in space, and they are non-interconvertible without the breaking of a covalent bond. In the practice of the invention, configurational isomers can be interconverted by, for example, breaking and optionally reforming disulfide bonds.

Thus, in one aspect, the invention entails contacting a preparation of the glycosylated recombinant protein that contains a mixture of at least two configurational isomers of the recombinant protein to a reduction/oxidation coupling reagent for a time sufficient to increase the relative proportion of the desired configurational isomer and determining the relative proportion of the desired configurational isomer in the mixture. In another aspect, the invention entails contacting a preparation of a recombinant protein that has been produced by mammalian cells with a reduction/oxidation coupling reagent, at a pH of about 7 to about 11, and isolating a fraction of the preparation of the recombinant protein with a desired conformation. Preferred recombinant proteins are glycosylated recombinant proteins such as, e.g., those produced by eukaryotic cells.

The invention can be used to treat just about any protein to promote a desired conformation. A protein is generally understood to be a polypeptide of at least about 10 amino acids, more preferably at least about 25 amino acids, even more preferably at least about 75 amino acids, and most preferably at least about 100 amino acids. The methods of the invention find particular use in treating proteins that have at least about 3 cysteine residues, more preferably at least about 8 cysteine residues, still more preferably at least about 15 cysteine residues, yet even more preferably at least about 30, still even more preferably at least about 50 to 150 cysteine residues.

Generally, the methods of the invention are useful for improving production processes for recombinant proteins. Recombinant proteins are proteins produced by the process of genetic engineering. The term "genetic engineering" refers to any recombinant DNA or RNA method used to create a host cell that expresses a gene at elevated levels, at lowered levels, and/or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96 (6):2758-63).

The invention finds particular use in improving the production of proteins that are glycosylated. Specifically, proteins that are secreted by fungal cell systems (e.g., yeast, filamentous fungi) and mammalian cell systems will be glycosylated. Preferably, the proteins are secreted by mammalian production cells adapted to grow in cell culture. Examples of such cells commonly used in the industry are CHO, VERO, BHK, HeLa, CV1 (including Cos), MDCK, 293, 3T3, myeloma cell lines (especially murine), PC12 and WI38 cells. Particularly preferred host cells are Chinese hamster ovary (CHO) cells, which are widely used for the production of several complex recombinant proteins, e.g. cytokines, clotting factors, and antibodies (Brasel et al., 1996, Blood 88:2004-2012; Kaufman et al., 1988, J. Biol Chem 263: 6352-6362; McKinnon et al., 1991, J Mol Endocrinol 6:231-239; Wood et al., 1990, J. Immunol 145:3011-3016). The dihydrofolate reductase (DHFR)-deficient mutant cell line (Urlaub et al., 1980, Proc Natl Acad Sci USA 77:4216-4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527-566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

It has been found that the invention is a gentle and effective process for improving the production process for proteins that can adopt multiple conformations and/or contain more than one domain. A "domain" is a contiguous region of the polypeptide chain that adopts a particular tertiary structure and/or has a particular activity that can be localized in that region of the polypeptide chain. For example, one domain of a protein can have binding affinity for one ligand, and one domain of a protein can have binding affinity for another ligand. In a thermostable sense, a domain can refer to a cooperative unfolding unit of a protein. Such proteins that contain more than one domain can be found naturally occurring as one protein or genetically engineered as a fusion protein. In addition, domains of a polypeptide can have subdomains.

In one aspect, the methods of the invention can be used on preparations of recombinant proteins in which at least one domain of the protein has a stable conformation, and at least one domain of the protein has an unstable conformation. The terms "stable" and "unstable" are used as relative terms. The domain of the protein with a stable conformation will have, for example, a higher melting temperature (Tm) than the unstable domain of the protein when measured in the same solution. A domain is stable compared to another domain when the difference in the Tm is at least about 2° C., more preferably about 4° C., still more preferably about 7° C., yet more preferably about 10° C., even more preferably about 15° C., still more preferably about 20° C., even still more preferably about 25° C., and most preferably about 30° C., when measured in the same solution.

The invention is also generally applicable to proteins that have an Fc domain, and another domain (e.g., antibodies, and Fc fusion proteins). For example, in one of the non-limiting embodiments illustrated below, TNFR:Fc, the Tm's for the Fc portion of the molecule are at 69.1° C. and 83.4° C., while the Tm for the TNFR portion of the molecule range from 52.5° C. (in the more desired conformation) to a Tm of 49.7° C. (in the less desired conformation).

Particularly preferred proteins are protein-based drugs, also known as biologics. Preferably, the proteins are expressed as extracellular products. Proteins that can be produced using the methods of the invention include but are not limited to a flt3 ligand (as described in WO 94/28391, which is incorporated by reference herein in its entirety), a CD40 ligand (as described in U.S. Pat. No. 6,087,329, which is incorporated by reference herein in its entirety), erythropoeitin, thrombopoeitin, calcitonin, Fas ligand, ligand for receptor activator of NF-kappa B (RANKL), tumor necrosis factor (TNF)-related apoptosis-inducing ligand (TRAIL, as described in WO 97/01633, which is incorporated by reference herein in its entirety), thymic stroma-derived lymphopoietin, granulocyte colony stimulating factor, granulocyte-macrophage colony stimulating factor (GM-CSF, as described in Australian Patent No. 588819, which is incorporated by reference herein in its entirety), mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of proteins that can be purified according to the inventive methods may be found in, for example, *Human Cytokines: Handbook for Basic and Clinical Research*, Vol. II (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991).

Preparations of the receptors, especially soluble forms of the receptors, for any of the aforementioned proteins can also be improved using the inventive methods, including both forms of TNFR (referred to as p55 and p75), Interleukin-1 receptors types I and II (as described in EP 0 460 846, U.S. Pat. No. 4,968,607, and U.S. Pat. No. 5,767,064, which are incorporated by reference herein in their entirety), Interleukin-2 receptor, Interleukin-4 receptor (as described in EP 0 367 566 and U.S. Pat. No. 5,856,296, which are incorporated by reference herein in their entirety), Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK, as described in U.S. Pat. No. 6,271,349, which is incorporated by reference herein in its entirety), receptors for TRAIL (including TRAIL receptors 1, 2, 3, and 4), and receptors that comprise death domains, such as Fas or Apoptosis-Inducing Receptor (AIR).

Other proteins whose production processes can be improved using the inventive methods include cluster of differentiation antigens (referred to as CD proteins), for example, those disclosed in *Leukocyte Typing VI* (*Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Proteins that are enzymatically active can also be prepared according to the instant invention. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be expressed by applying the instant invention.

The inventive compositions and methods are also useful for preparation of other types of recombinant proteins, including immunoglobulin molecules or portions thereof, and chimeric antibodies (e.g., an antibody having a human constant region coupled to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397). Preparations of fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. The method of the invention may also be used during the preparation of conjugates comprising an antibody and a cytotoxic or luminescent substance. Such substances include: maytansine derivatives (such as DM1); enterotoxins (such as a *Staphlyococcal* enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6).

Examples of antibodies or antibody/cytotoxin or antibody/luminophore conjugates contemplated by the invention include those that recognize any one or combination of the above-described proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-4, IL-5, IL-8, IL-10, IL-2 receptor, IL-4 receptor, IL-6 receptor, IL-13 receptor, IL-18 receptor subunits, PDGF-β, VEGF, TGF, TGF-β2, TGF-β1, EGF receptor, VEGF receptor, CS complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human imillimolarunodeficiency virus (HIV), hepatitis B virus (HBV), *Streptococcus mutans*, and *Staphlycoccus aureus*.

Preparations of various fusion proteins can also be prepared using the inventive methods. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the above molecules can be expressed as a fusion protein including but not limited to the extracellular domain of a cellular receptor molecule, an enzyme, a hormone, a cytokine, a portion of an immunoglobulin molecule, a zipper domain, and an epitope.

The preparation of recombinant protein can be a cell culture supernatant, cell extract, but is preferably a partially purified fraction from the same. By "partially purified" means that some fractionation procedure, or procedures, have been carried out, but that more polypeptide species (at least 10%) than the desired protein or protein conformation is present. One of the advantages of the methods of the invention is that the preparation of recombinant protein can be at a fairly high concentration. Preferred concentration ranges are 0.1 to 20 mg/ml, more preferably from 0.5 to 15 mg/ml, and still more preferably from 1 to 10 mg/ml.

The preparation of recombinant protein can be prepared initially by culturing recombinant host cells under culture conditions suitable to express the polypeptide. The polypeptide can also be expressed as a product of transgenic animals, e.g., as a component of the milk of transgenic cows, goats, pigs, or sheep which are characterized by somatic or germ cells containing a nucleotide sequence encoding the polypeptide. The resulting expressed polypeptide can then be purified, or partially purified, from such culture or component (e.g., from culture medium or cell extracts or bodily fluid) using known processes. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

For example, the purification of the polypeptide can include an affinity column containing agents which will bind to the polypeptide; one or more column steps over such affinity resins as concanavalin A-agarose, heparin-toyopearl® or Cibacrom blue 3GA Sepharose®; one or more steps involving elution; and/or immunoaffinity chromatography. The polypeptide can be expressed in a form that facilitates purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope (FLAG®) is commercially available from Kodak (New Haven, Conn.). It is also possible to utilize an affinity column comprising a polypeptide-binding polypeptide, such as a monoclonal antibody to the recombinant protein, to affinity-purify expressed polypeptides. Other types of affinity purification steps can be a Protein A or a Protein G column, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety. In one embodiment of the invention illustrated below, the preparation of recombinant protein has been partially purified over a Protein A affinity column.

Some or all of the foregoing purification steps, in various combinations, can also be employed to prepare an appropriate preparation of a recombinant protein for use in the methods of the invention, and/or to further purify the recombinant polypeptide after contacting the preparation of the recombinant protein with a reduction/oxidation coupling reagent. The polypeptide that is substantially free of other mammalian polypeptides is defined as an "isolated polypeptide".

The polypeptide can also be produced by known conventional chemical synthesis. Methods for constructing polypeptides by synthetic means are known to those skilled in the art. The synthetically-constructed polypeptide sequences can be glycosylated in vitro.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, and/or (if the polypeptide is radiolabeled) by autoradiography.

By "contacting" is meant subjecting to, and/or exposing to, in solution. The protein or polypeptide can be contacted while also bound to a solid support (e.g., an affinity column or a chromatography matrix). Preferably, the solution is buffered. In order to maximize the yield of protein with a desired conformation, the pH of the solution is chosen to protect the stability of the protein and to be optimal for disulfide exchange. In the practice of the invention, the pH of the solution is preferably not strongly acidic. Thus, preferred pH ranges are greater than pH 5, preferably about pH 6 to about pH 11, more preferably from about pH 7 to about pH 10, and still more preferably from about pH 7.6 to about pH 9.6. In one non-limiting embodiment of the invention using TNFR: Fc that is illustrated below, the optimal pH was found to be about pH 8.6. However, the optimal pH for a particular embodiment of the invention can be easily determined experimentally by those skilled in the art.

The reduction/oxidation coupling reagent is a source of reducing agents. Preferred reducing agents are free thiols. The reduction/oxidation coupling reagent is preferably comprised of a compound from the group consisting of reduced and oxidized glutathione, dithiothreitol (DTT), 2-mercaptoethanol, dithionitrobenzoate, cysteine and cystine. For ease of use and economy, reduced glutathione and/or reduced cysteine can be used.

The reduction/oxidation coupling reagent is present at a concentration sufficient to increase the relative proportion of the desired conformation. The optimal concentration of the reduction/oxidation coupling reagent depends upon the concentration of protein and number of disulfide bonds in the protein. For example, it has been found using a protein (TNFR:Fc) with 29 disulfide bonds at a concentration of 2 mg/ml (approximately 14 microM protein or 400 microM disulfide), a reduction/oxidation coupling reagent with 2 mM reduced thiols worked well to increase the relative proportion of the desired conformation. This corresponds to a ratio of about 35 free thiols to 1 disulfide bond. However, it was also found that ratios from 20 to 400 free thiols per disulfide also worked. Of course, the amount of thiol used for a particular concentration can vary somewhat depending upon the reducing capacity of the thiol, and can be easily determined by one of skill in the art.

Thus, generally, the concentration of free thiols from the reduction/oxidation coupling reagent can be from about 0.05 mM to about 50 mM, more preferably about 0.1 mM to about 25 mM, and still more preferably about 0.2 mM to about 20 mM.

In addition, the reduction/oxidation coupling reagent can contain oxidized thiols at approximately higher, equal or lower concentrations as the reduced thiol component. For example, the reduction/oxidation coupling reagent can be a combination of reduced glutathione and oxidized glutathione. It has been found through actual working examples, that a ratio of reduced glutathione to oxidized glutathione of from about 1:1 to about 100:1 (reduced thiols:oxidized thiols) can function equally well. Alternatively in another embodiment, the reduction/oxidation coupling reagent can be cysteine or a combination of cysteine and cystine. Thus, when oxidized thiols are included in the initial reduction/oxidation coupling reagent, the ratio of reduced thiols to oxidized thiols can in a preferred embodiment be from about 1:10 to about 1000:1, more preferably about 1:1 to about 500:1, still more preferably about 5:1 to about 100:1, even more preferably about 10:1.

Contacting the preparation of recombinant protein with a reduction/oxidation coupling reagent is performed for a time sufficient to increase the relative proportion of the desired conformation. Any relative increase in proportion is desirable, but preferably at least 10% of the protein with an undesired conformation is converted to protein with the desired conformation. More preferably at least 20%, 30%, 40%, 50%, 60%, 70% and even 80% of the protein is converted from an undesired to a desired conformation. Typical yields that have been achieved with the methods of the invention range from 40 to 80%. If the contacting step is performed on a partially or highly purified preparation of recombinant protein, the contacting step can be performed for as short as about 1 hour to about 4 hours, and as long as about 6 hours to about 4 days. It has been found that a contacting step of about 4 to about 16 hours or about 18 hours works well. The contacting step can also take place during another step, such as on a solid phase or during filtering or any other step in purification.

The methods of the invention can be performed over a wide temperature range. For example, the methods of the invention have been successfully carried out at temperatures from about 4° C. to about 37° C., however the best results were achieved at lower temperatures. A typical temperature for contacting a partially or fully purified preparation of the recombinant protein is about 4° C. to about 25° C. (ambient), but can also be performed at lower temperatures and at higher temperature.

The preparation of recombinant protein can be contacted with the reduction/oxidation coupling reagent in various volumes as appropriate. For example, the methods of the invention have been carried out successfully at the analytical laboratory-scale (1-50 mL), preparative-scale (50 mL-10 L) and manufacturing-scale (10 L or more). Thus, the methods of the invention can be carried out on both small and large scale with reproducibility.

In preferred aspects, the contacting step is performed in the absence of significant amounts of chaotropic agents such as, for example, SDS, urea and guanidium HCl. Significant amounts of chaotropic agents are needed to observe perceptible unfolding. Generally, less than 1 M chaotrope is present, more preferably less than 0.5 M, still more preferably less than 0.1 M chaotrope. A solution is essentially free of chaotrope (e.g., SDS, urea and guanidium HCl) when no chaotrope has been purposely added to the solution, and only trace levels (e.g., less than 10 mM) may be present (e.g., from the vessel or as a cellular byproduct).

Disulfide exchange can be quenched in any way known to those of skill in the art. For example, the reduction/oxidation coupling reagent can be removed or its concentration reduced through a purification step, and/or it can be chemically inactivated by, e.g., acidifying the solution. Typically, when the reaction is quenched by acidification, the pH of the solution containing the reduction/oxidation coupling reagent will be brought down below pH 7. Preferably, the pH is brought to below pH 6. Generally, the pH is reduced to between about pH 2 and about pH 7.

Determining the conformation of a protein, and the relative proportions of a conformation of a protein in a mixture, can be done using any of a variety of analytical and/or qualitative techniques. If there is a difference in activity between the conformations of the protein, determining the relative proportion of a conformation in the mixture can be done by way of an activity assay (e.g., binding to a ligand, enzymatic activity, biological activity, etc.). For example, in one of the non-limiting embodiments described below, at least two different conformations of TNFR:Fc can be resolved by using a solid-phase TNF binding assay. The assay, essentially as described for IL-1R (Slack, et al., 1993, J. Biol. Chem. 268: 2513-2524), can differentiate between the relative proportions of various protein conformations by changes in ligand-receptor binding association, dissociation or inhibition constants generated. Alternatively the binding results can be expressed as activity units/mg of protein.

If the two conformations resolve differently during chromatography, electrophoresis, filtering or other purification technique, then the relative proportion of a conformation in the mixture can be determined using such purification techniques. For example, in the non-limiting embodiments described below, at least two different conformations of TNFR:Fc could be resolved by way of hydrophobic interaction chromatography. Further, since far-UV Circular Dichroism has been used to estimate secondary structure composition of proteins (Perczel et al., 1991, Protein Engrg. 4:669-679), such a technique can determine whether alternative conformations of a protein are present. Still another technique used to determine conformation is fluorescence spectroscopy which can be employed to ascertain complimentary differences in tertiary structure assignable to tryptophan and tyrosine fluorescence. Other techniques that can be used to determine differences in conformation and, hence, the relative proportions of a conformation, are on-line SEC to measure aggregation status, differential scanning calorimetry to measure melting transitions (Tm's) and component enthalpies, and chaotrope unfolding.

By the term "isolating" is meant physical separation of at least one component in a mixture away from other components in a mixture. Isolating components or particular conformations of a protein can be achieved using any purification method that tends to separate such components. Accordingly, one can perform one or more chromatography steps, including but not limited to HIC, hydroxyapatite chromatography, ion exchange chromatography, affinity, and SEC. Other purification methods are filtration (e.g., tangential flow filtration), electrophoretic techniques (e.g., electrophoresis, electroelution, isoelectric focusing), and phase separation (e.g., PEG-dextran phase separation), to name just a few. In addition, the fraction of the preparation of recombinant protein that contains the protein in the undesired conformation can be treated again in the methods of the invention, to further optimize the yields of protein with the desired conformation.

For example, after treatment, protein samples can be prepared for hydrophobic interaction chromatography (HIC) by the following method. An equal volume of 850 mM sodium citrate, 50 mM sodium phosphate, pH 6.5 is added to the treated sample, and allowed to equilibrate to room temperature. After filtering (e.g., using a 0.22 □m filter), HIC chromatography is performed on a Toyopearl® Butyl 650-M resin (Tosoh Biosep LLC, Montgomeryville, Pa.), at a flow rate of 150 cm/hr, and a mass load of 2.1 mg·mL resin$^{-1}$. The column is prequilibrated with 3 column volumes of 425 mM NaCitrate, 50 mM PO$_4$ pH 6.5, sample is loaded, and then washed through with 3 column volumes of 425 mM NaCitrate, 50 mM PO$_4$ pH 6.5. Elution can be performed with a gradient of 425 mM NaCitrate, 50 mM PO$_4$ pH 6.5 to O mM NaCitrate, 50 mM PO$_4$ pH 6.5 in a total of 5 column volumes. Fractions can be collected during the elution. The column can be stripped with 3 column volumes of water followed by 3 column volumes of 0.1M NaOH. Using the methods of the invention accordingly, one can thus obtain preparations of TNFR:Fc that contain more than 85%, more than 90%, and even more than 95% of the TNFR:Fc present in the preparation in the most active conformation (Fraction #2). Compositions, including pharmaceutical compositions, of TNFR:Fc containing such proportions of Fraction #2 are therefore also provided by the invention.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption.

Such compositions can comprise an effective amount of the protein, in combination with other components such as a physiologically acceptable diluent, carrier, and/or excipient. The term "pharmaceutically acceptable" means a non-toxic material that does not interfere with the effectiveness of the biological activity of the active ingredient(s). Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. In addition, sterile bulk forms and sterile unit forms may contain a small concentration (approximately 1 microM to approximately 10 mM) of a reduction/oxidation coupling reagent (e.g., glutathione, cysteine, etc.). The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences*, 16th ed. 1980, Mack Publishing Company, Easton, Pa. In addition, such compositions can be complexed with polyethylene glycol (PEG), metal ions, and/or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The invention having been described, the following examples are offered by way of illustration, and not limitation.

EXAMPLE 1

Biophysical Assessment of TNFR:Fc Fractions #2 and #3

TNFR:Fc elutes off a hydrophobic interaction column (HIC) as three distinct peaks termed Fraction #1, Fraction #2 and Fraction #3 (see FIG. 1). Fraction #2 is the desired fraction. Fraction #3 was of particular interest since it can comprise from 20 to 60% of the sample and has been shown to exhibit low TNF binding activity and A375 bioactivity in comparison with Fraction #2. Therefore, in the interest of understanding the differences between these two fractions and ascertaining what factors contribute to the loss in activity for Fraction #3 as it pertains to structure and conformation, biophysical studies were carried out. In this example, we analyzed Fraction #2 and Fraction #3 using Circular Dichroism, Fluorescence, on-line SEC/UV/LS/RI, and differential scanning calorimetry (DSC).

Materials and Methods:

Materials: The starting material was TNFR:Fc in TMS buffer (10 mM Tris, 4% mannitol, 1% sucrose). HIC eluted fractions of this material were isolated as Fractions #2 and #3 for experimental studies described below.

Circular Dichroism: Studies were carried out in the near (250-340 nm) and far-UV (190-250 nm) regions. The near-UV studies were carried out to elucidate differences in tertiary structure while the far-UV studies were used to characterize differences in secondary structure.

The near-UV Circular Dichroism measurements were conducted in the TMS solutions with the following concentrations. Starting material was diluted to 6.25 mg/ml while the Fractions #2 and #3 were evaluated at their existing concentrations of 9.4 and 5.4 mg/ml, respectively. A Circular Dichroism cell with a path length of 0.1 cm was used and scans conducted from 340 to 250 nm.

The far-UV Circular Dichroism measurements were performed with the protein buffer exchanged into 10 mM sodium phosphate (pH 7.0) and subsequently evaluated using a 0.1 cm path length cell scanned from 250 to 190 nm. Secondary structure composition was evaluated using convex constraint analysis (CCA) (Perczel et al., 1991, Protein Engrg. 4:669-679).

Fluorescence Spectroscopy: Samples were examined after dilution to approximately 50 microgram/ml using two different excitation wavelengths. Tyrosine and tryptophan fluorescence was examined with an excitation of 270 nm while tryptophan fluorescence was exclusively evaluated using an excitation of 295 nm (Lakowicz, J. R. in "Principles of Fluorescence Spectroscopy", Plenum Press, 1983. New York, N.Y., 342-343). Fluorescence scans extended from 300 to 440 nm for 270 nm excitation and from 310 to 440 nm for 295 nm excitation. Four consecutive scans were signal averaged for each spectrum. Normalized data were reported to evaluate differences in frequency arising from the samples.

Online-SEC/UV/LS/RI: The molecular weights of eluting components using size exclusion chromatography were ascertained using ultraviolet (UV @ 280 nm), light scattering (90°), and refractive index (RI) detection in series. This method has been well documented (see Arakawa et al., 1992, Anal. Biochem. 203:53-57 and Wen et al., 1996, Anal. Biochem. 240:155-166), and has an advantage of measuring the nonglycosylated molecular weights of proteins and peptides that are glycosylated. The SEC and UV data were collected using an Integral HPLC system (PerSeptive Biosystems, Inc.) with a BioSil-400-5 column (from BioRad) using a flow rate of 1 ml/min. The elution buffer consisted of 100 mM phosphate (pH 6.8) and 100 mM NaCl. A DAWN DSP multi-angle light scattering detector and Optilab DSP refractometer were both purchased from Wyatt Technology, Inc. Calibration standards to determine instrumental constants included BSA dimer, BSA monomer and ovalbumin (FIG. 2).

Differential Scanning Calorimetry (DSC): Physical properties of unfolding were measured using a MicroCal MC-2 DSC instrument in upscan mode. Samples were prepared by buffer exchanging into the same TMS buffer at pH 7.4. Samples contained about 4 mg/ml protein and were evaluated against the buffer (absent protein) as a reference. The scan rate was 67° C./hr spanning the temperature regime from 20° C. to 90° C. Collected scans were subsequently converted into concentration normalized scans to better compare enthalpic behavior of unfolding transitions while taking into account differences in concentration (data reported as kcal/mole).

Figure 2A:
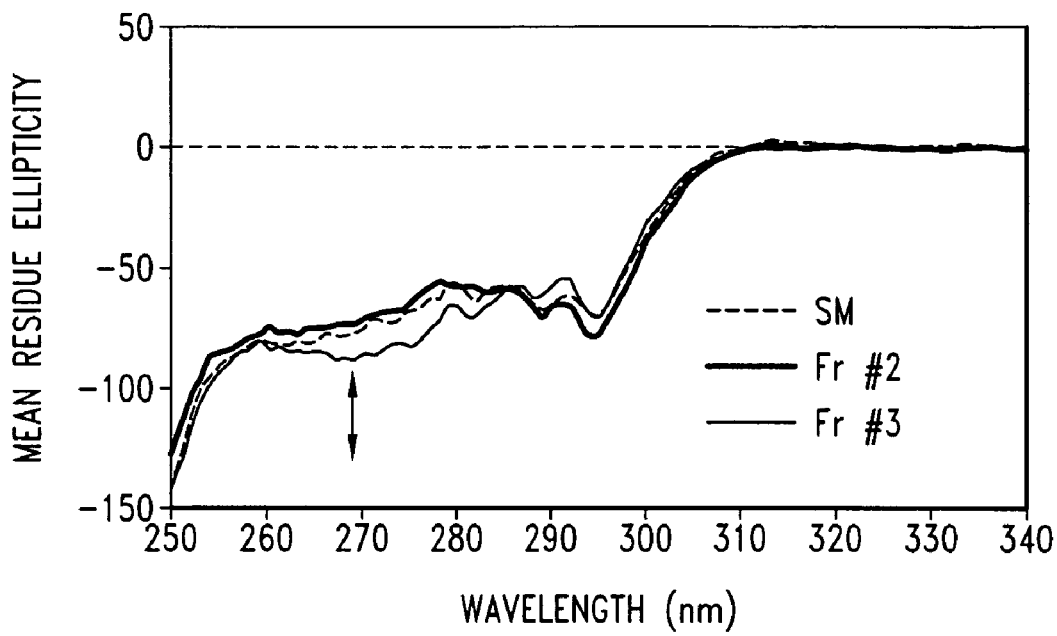
FIG. 2A presents the spectral data; The line for Fraction #3 is closest to the arrow highlighting the negative displacement at about 270 nM ascribed to disulfide contributions, and the line for Fraction #2 is the darker solid line.
Figure 2B:
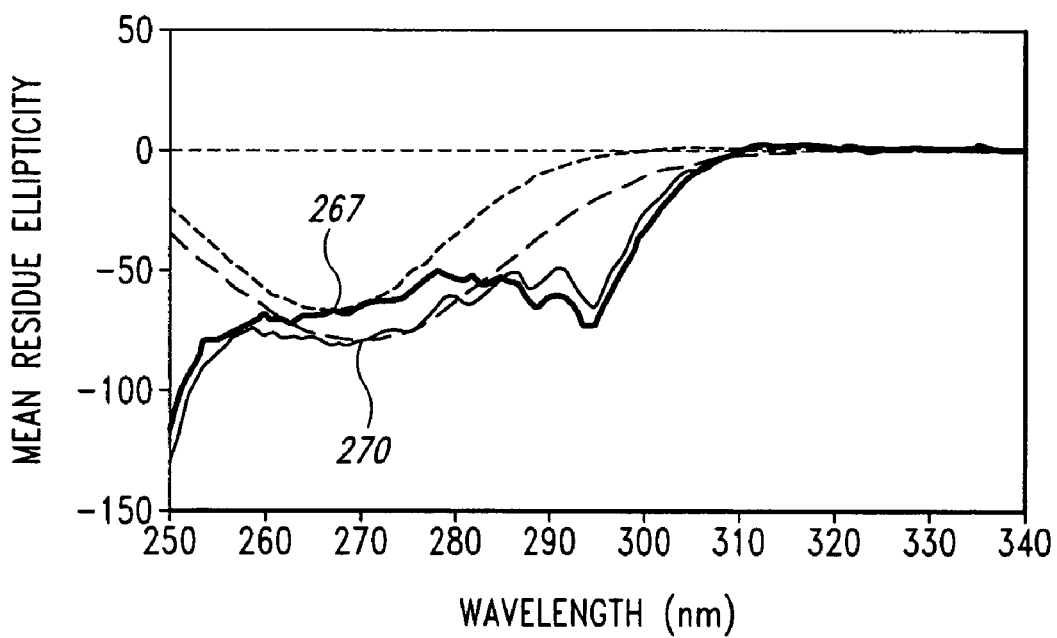
FIG. 2B presents the curve-fitted data for Fraction #2 (small dashed line) and Fraction #3 (larger dashed line).

Results:

Circular Dichroism. The near-UV Circular Dichroism measurements expressed in terms of mean residue ellipticity are shown in FIG. 2. Changes in a broad feature near 270 nm were evident between Fraction #2 and #3 as shown by a greater proportion of negative ellipticity in the spectrum of Fraction #3 (indicated by the arrow in FIG. 2A). It was noted that the spectral behavior of the starting material closely matches that of Fraction #2 but does exhibit a subtle negative displacement in the same region surrounding 270 nm. This result seemed consistent as Fraction #3 made up a small part of the starting material and so its contribution to the overall ellipticity in this region was greatly reduced but in the same displacement direction. Reproducibility of the Fraction #3 spectrum confirmed the observed displacement of this sample to be real. With this in mind, and knowing that disulfides give rise to a broad negative elliptical feature in this region of the Circular Dichroism spectrum (see Kahn, P. C., 1978, Methods Enzymol. 61:339-378 and Kosen et al., 1981, Biochemistry 20:5744-5754), the near-UV Circular Dichroism spectrum was curve-fitted to estimate what the observed changes in this region mean in terms of tertiary structure. The results of the curve-fitted data are presented in FIG. 2B and showed a small red-shift (3 nm) and enhanced negative displacement consistent with the contribution arising from a change in tertiary structure involving disulfides when comparing Fraction #3 with #2.

The far-UV Circular Dichroism has been used to estimate secondary structure composition of proteins (Perczel et al., 1991, Protein Engrg. 4:669-679). Secondary structure assignments using CCA were performed. Calculated spectra comprised of the sum of the secondary structure elements were compared with experimentally observed spectra and exhibited a good fit. The secondary structures of both fractions were comparable within limits of experimental precision (within 10%). Therefore, this experiment did not distinguish any differences regarding secondary structure for either of these two fractions.

Fluorescence Spectroscopy. Knowing that there were significant differences observed in the near-UV Circular Dichroism region, fluorescence spectroscopy was employed to ascertain complimentary differences in tertiary structure assignable to tryptophan and tyrosine fluorescence. Using two excitation wavelengths, it was possible to determine that the spectra for all three cases considered (SM, Fraction #2 and #3) were super-imposable with fluorescence maxima near 338 nm. Since the three-dimensional structure of a given protein is responsible for emission maxima of native proteins, these results suggested that the average structure involving the intrinsic fluorophores, tryptophan and tyrosine was unperturbed.

Figure 3A:
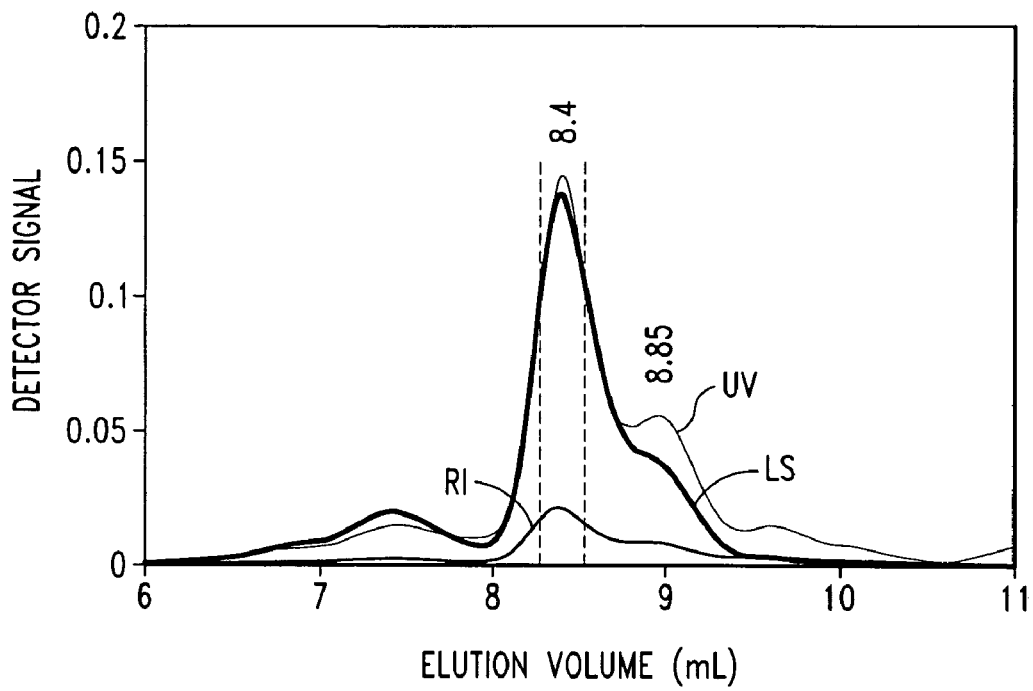
FIG. 3A is Fraction #3.
Figure 3B:
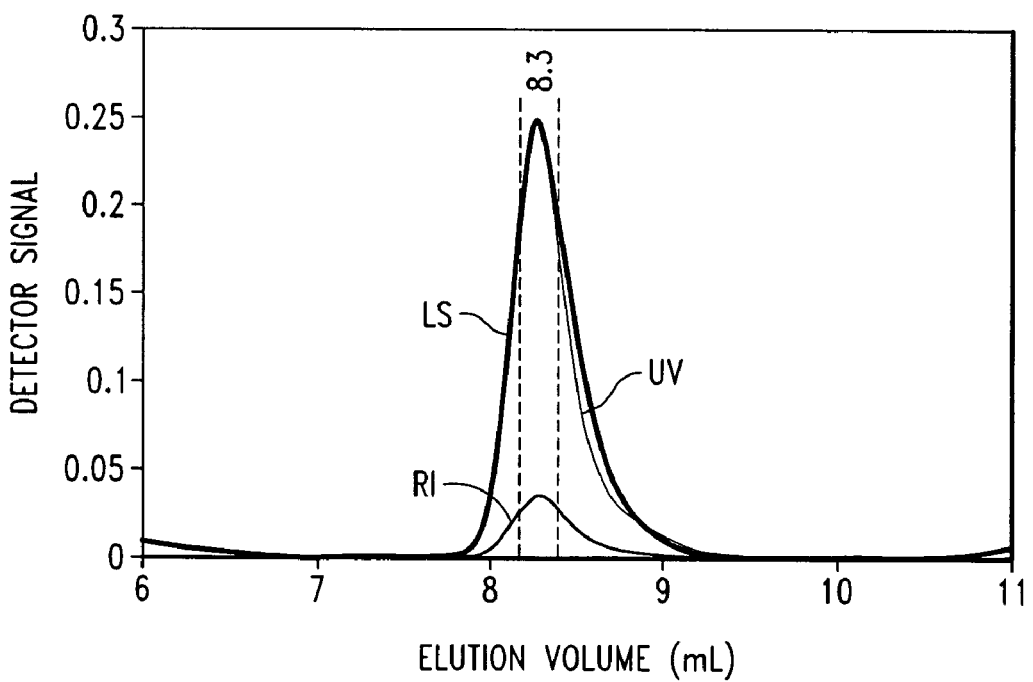
FIG. 3B is Fraction #2. Vertical dashed lines indicate where the slices were evaluated for molecular weight determination in the region surrounding the main peak.

On-line SEC/UV/LS/RI. The light scattering studies performed on-line with SEC yielded molecular weights of the main elution peak that were in agreement with the non-glycosylated polypeptide molecular weight of TNFR:Fc (e.g., 102 kD). Although there were clear differences in the compositions of eluting species evaluated with this technique, when comparing the elution profile of Fraction #3 with Fraction #2 (FIG. 3A and B), the main peak comprising the majority component was measured to be 102.5±1.6 kD (Retention Volume=8.4 mL) and 101.9±2.1 kD (Retention Volume=8.3 mL), respectively. The precision was expressed as the standard deviation of 23 slices through the elution peak bracketed by the vertical dashed lines in FIG. 3. It was also noted that a respectable signal of the descending shoulder for Fraction #3 permitted determination of the polypeptide molecular weight to be 78.1±3.7 kD (this evaluation considered 8 slices surrounding the peak labeled at 8.85 mL). As exhibited by the precision associated with the molecular weight determination of this component, this peak exhibited greater heterogeneity and as a result was suspect of greater polydispersion than the main peak. Fraction #3 also contained a significant amount of high molecular weight species consistent with the elution volume of a predominantly dimeric form of TNFR:Fc (near 7.5). Hence, it was determined that Fraction #3 is comprised of several species including aggregates and fragmented portions of the molecule.

Figure 4A:
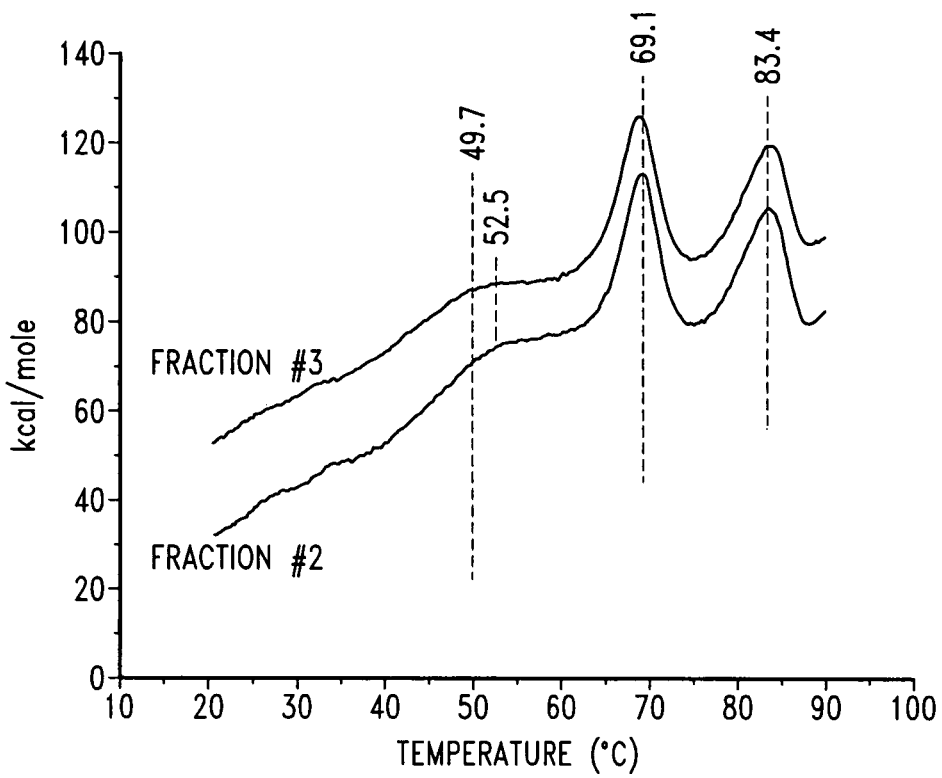
FIG. 4A is the uncorrected data.
Figure 4B:
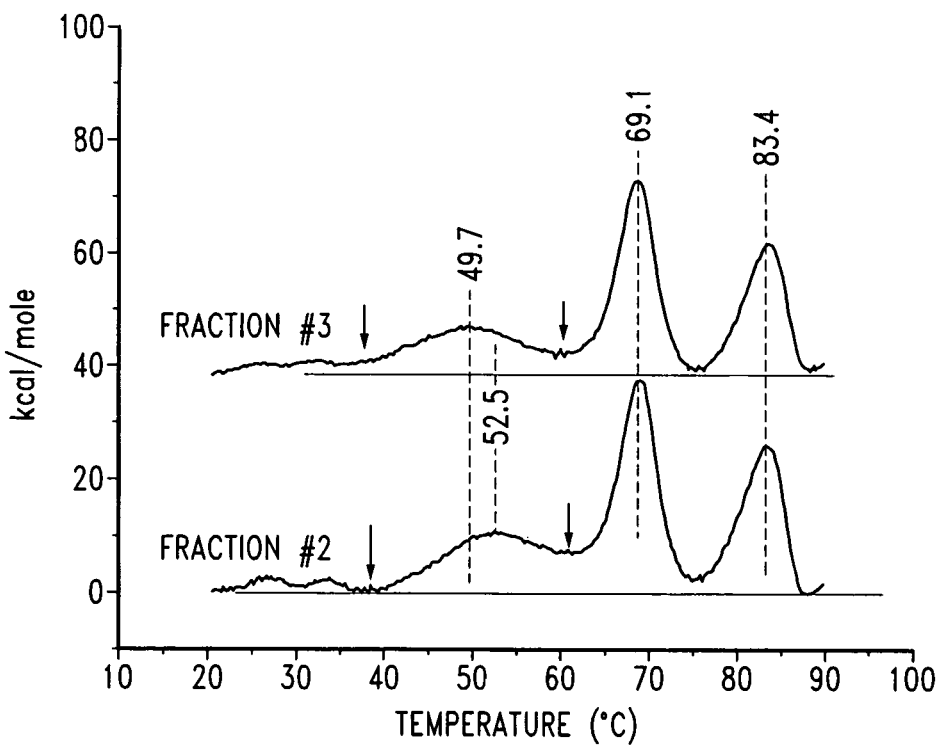
FIG. 4B presents the baseline-corrected data. Thermal melting transitions are labeled by vertical dashed lines. Arrows indicate an enthalpy displacement. The horizontal dotted lines in FIG. 4B are used as a baseline reference.

Differential Scanning Calorimetry. DSC measurements carried out on the two fractions yielded significant differences in the unfolding of the TNFR moiety of the TNFR:Fc molecule (FIG. 4). As shown more clearly in the baseline corrected data (FIG. 4B), there is a 2.8° C. shift to lower temperature in the melting transition (Tm) when comparing a Tm of 52.5° C. (Fraction #2) with a Tm of 49.7° C. (Fraction #3). The transition is slightly broader for Fraction #3 with a half-width at half the transition maximum of 8° C. in comparison with Fraction #2 having a half-width of 6.5° C. This low temperature transition has been identified from thermal unfolding experiments of TNFR:Fc monomer to be due the TNFR domain of the molecule. Thermal transitions at 69.1° C. and 83.4° C. have been assigned to the Fc portion of the molecule. These latter two unfolding transitions align well and are comparable in terms of Tm's and component enthalpies.

Discussion:

Among the methods tested, differences were observed in the near-UV Circular Dichroism and DSC measurements. Differential scanning calorimetry data support a loosening of structure that is assignable to the receptor moiety of the molecule with little change observed in the region of the Fc. The near-UV Circular Dichroism results suggested that disulfides are involved with tertiary structural changes associated with Fraction #3. These changes may arise as a consequence of buried disulfides gaining more exposure to the solvent and account for an increase in hydrophobicity as suggested by the small increase in retention time observed in the HIC elution of Fraction #3. It is interesting that there are no discernible differences found in the fluorescence data that would indicate such a change in conformational structure. If one considers the primary structure of TNFR:Fc in terms of the distribution of tyrosines (Y) and tryptophans (W), it becomes apparent that the region extending from the C-terminal portion of residue 104 of the TNFR domain to residue 296 of the N-terminal portion of the Fc (comprising 40% of the linear sequence of TNFR:Fc) is devoid of these intrinsic fluorophores. Therefore, one possible explanation consistent with the data might be that tertiary structure remote from the Fc hinge region is relatively unchanged while that from about residue C115 to C281 may be somewhat altered conformationally. This region of the molecule comprises 10 possible cysteines that may be affected with supposedly little consequence of structural change affecting local structure of tyrosines and tryptophans. It is noted that it is currently unknown as to how this molecule is folded and it would seem plausible that the cysteines that make up disulfides that are more remote from any given tryptophan or tyrosine residue would be logical suspects for tertiary structural changes that produce the observed near-UV Circular Dichroism results but exhibit little impact on the vicinal structure involving tyrosines and tryptophans. This idea does not preclude the possibility that there is some unusual change in structure within one or both of the TNFR arms that does not invoke an appreciable change in the net effect of fluorescence arising from tyrosines and tryptophans. The fact that the fluorescence data (which is insensitive to disulfides) show no change and the near-UV (that is sensitive to disulfides, tyrosines, and tryptophans) exhibits a small negative displacement consistent with disulfide structural modification does imply that disulfides play a role in the difference between Fractions #2 and #3.

In summarizing the remaining data generated concerning Fraction #3, aspects related to molecular weight and secondary structure were found to be indistinguishable from the more active form (Fraction #2).

EXAMPLE 2

Disulfide Exchange Experiments on TNFR:Fc Fraction #3 with Glutathione

This experiment was designed to assess a variety of treatments to drive TNRF:Fc Fraction #3 into the conformation of Fraction #2 in a process amenable to large-scale production runs.

Materials and Methods:

Materials. The starting material was TNFR:Fc as a Protein A elute, a pure HIC elute of Fraction #3, and a 50:50 mixture of HIC elutes Fraction #2 and Fraction #3. Buffers were 0.1 M citrate or 0.1 M Tris/glycine at pH 7.6, pH 8.6 or pH 9.6. Protein concentration of the TNFR:Fc was from 0.2 to 4.5 mg/mL. A redox coupling system of reduced glutathione and glutathione (GSH/GSSG at a ratio of 10:1) was added at 0.1 to 5 mM GSH. Incubation temperature was varied at 4 degrees, 22 degrees or 31 degrees Centigrade.

Methods. Disulfide exchange was quenched by acidification of the sample to pH 6 with 1 M acetic acid. Treated preparations of recombinant protein were characterized by analytical HIC, SEC (retention time, aggregate concentration) and solid-phase TNF binding assay to determine the percentage and yield of Fraction #2.

Results and Discussion:

Treatment efficiency as a function of pH and GSH concentration. Significant % of the protein in Fraction #3 (at least 10%) was converted Fraction #2 when treatment was performed at both 0.1 mM GSH/pH 7.6 and 0.1 mM GSH/pH 8.6. However, efficiency was greatly improved (from 45% to almost 70%) when treatment was performed at 0.1 mM GSH/pH 9.6; 1 mM GSH/pH 7.6; 1 mM GSH/pH 8.6; and 1 mM GSH/pH 9.6. Thus, although treatment efficiency is sensitive to pH and free thiol concentration, it can be effectively performed over a wide range of these variables.

Temperature effects. Fraction #3 was treated at three different temperatures, 4° C., 22° C. and 31° C. The GSH concentration was held at 1 mM, and pH 8.6. After 16 hours, the treatment groups all exhibited significant conversion of Fraction #3 into Fraction #2, but conversion seemed slightly more efficient at the two lower temperatures.

Clone effects. Six different cell line clones, all producing TNFR:Fc, were tested in a standardized protocol based upon the above results. Specifically, a Protein A elution containing 0.4 to 0.7 mg/mL of TNFR:Fc (at about pH 4) was adjusted to pH 8.6 using 1M Tris/glycine (final concentration 0.1 M Tris/glycine). These solutions were adjusted to 1 mM EDTA and 2.5 mM GSH/0.25 mM GSSG and incubated at room temperature for about 16 hours. Disulfide exchange was quenched by acidification as described above.

Figure 5:
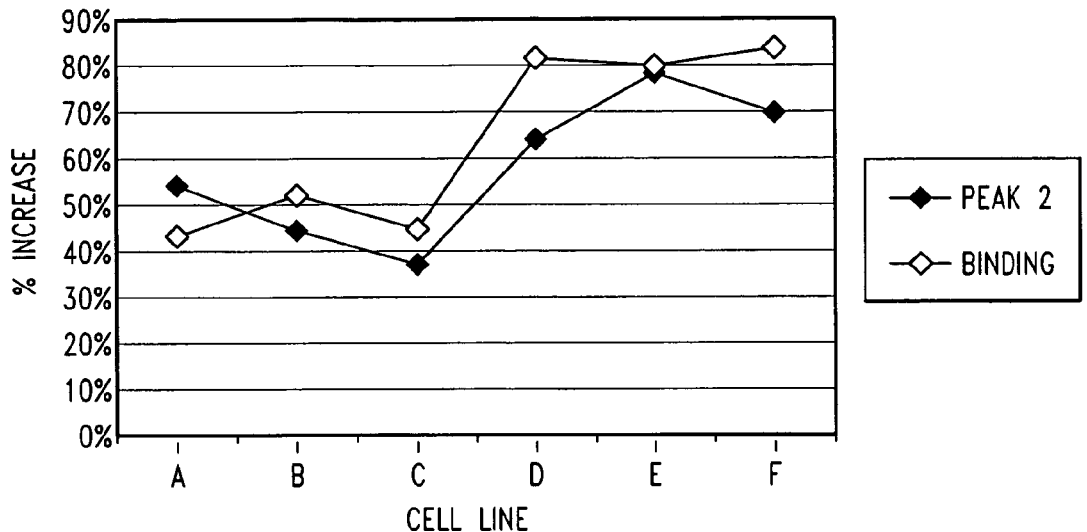
FIG. 5. Correlation of Fraction #2 and Binding Activity. Six different preparations of TNFR:Fc (denoted A through F), from six different cell lines, were tested for the correlation between the percent increase in proportion of Fraction #2 (dark diamonds) and percent increase in TNF alpha Binding Units (light diamonds).

Each of six different clones all showed improvement in production and yield of Fraction #2. The reduction of HIC Fraction #3 by treatment in the various clones was 64%, 72%, 77%, 78%, 78% and 83%. The increase in HIC Fraction #2 in the same clones was 37%, 64%, 78%, 70%, 44% and 54%, respectively. Percent increase in HIC Fraction #2 was well correlated with the % increase in Binding Units, as shown in FIG. 5. Thus, the methods appeared generally applicable across all clones tested.

Binding assays. Three different preparations of TNFR:Fc were assayed in a solid-phase TNF binding assay. Samples 11-6 and 12 were eluants from a Protein A column. Sample 8085-47 was also eluted from a Protein A column, and then subjected to an additional HIC purification step; this sample contained exclusively Fraction #3. Samples were examined in the binding assay before and after disulfide exchange as described above. The results presented below in Table 1 show an increase in ligand binding activity after treatment of all samples with glutathione.

TABLE 1

TNF binding activity of TNFR:Fc before and after disulfide exchange

| Sample | Pre-exchange (activity/mg of protein) | Post-exchange (activity/mg of protein) | % Change |
|---|---|---|---|
| 11-6 | $4.16 \times 10^7$ | $5.73 \times 10^7$ | 27% |
| 12 | $4.36 \times 10^7$ | $6.13 \times 10^7$ | 29% |
| 8085-47 | $1.90 \times 10^7$ | $6.75 \times 10^7$ | 72% |

EXAMPLE 3

Disulfide Exchange Experiments on TNFR:Fc Treated with L-Cysteine

This experiment was designed to assess cysteine/cystine as reduction/oxidation coupling reagents for TNFR:Fc. The procedure allows assessment of change of HIC Fraction #3 into the conformation of Fraction #2 in a process amenable to large-scale production runs. The procedure can be performed on a purified Fraction #3, a mixture of Fractions #2 and #3, and/or following other separation techniques such as Protein A chromatography, with similar results.

Materials and Methods:

The starting material was TNFR:Fc as a pure HIC elute of Fraction #3 or as a Protein A-eluted TNFR:Fc containing both Fraction #2 and #3. Buffers were 0.1 M citrate or 0.2 M Tris at pH 8.5. Protein concentration of the TNFR:Fc was 2.5 to 3 mg/mL.

A redox coupling system of L-cysteine (varying from 0 to 50 mM) was utilized. The procedure was also assessed +/−L-cystine (0.025 to 0.5 mM) and +/−1 mM EDTA. Incubation temperature was assessed at 4, 15, and 22 degrees Centigrade for 6, 18, and 48 hours. Disulfide exchange was quenched by acidification of the sample to pH 7 with $NaH_2PO_4$ or 0.85 M citrate. Treated preparations of recombinant protein were characterized by analytical HIC and SEC (retention time, aggregate concentration) to determine the percentage and yield of Fraction #2 and Fraction #3, cysteinylation and free sulfhydral assays.

Figure 6:
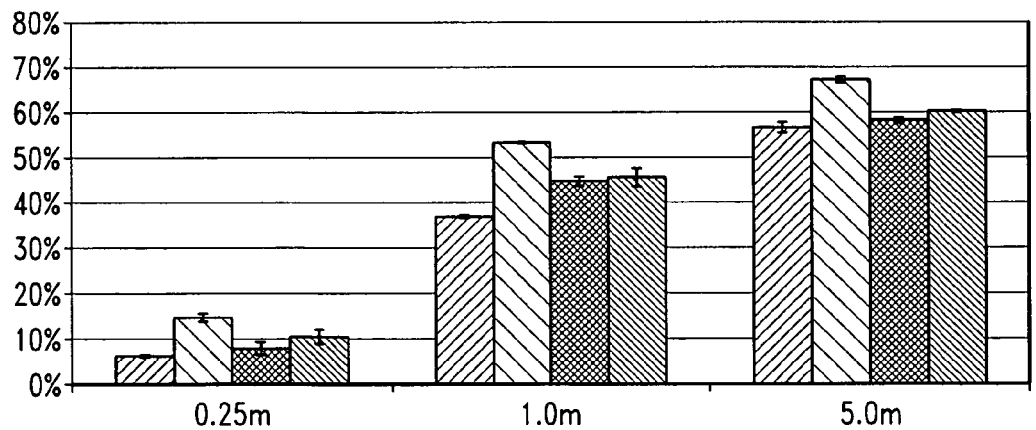
FIG. 6. Effect of Varying Cysteine Concentration on Conversion of Fraction #3 into Fraction #2. Protein samples were treated with various concentrations of cysteine (0.25-5.0 mM) and changes in Fraction #3 assessed using HIC. Four different lots of TNFR:Fc were treated for 18 hours at the indicated cysteine concentration on the x-axis. The percent of Fraction #3 in each lot that was converted into Fraction #2 is plotted on the y-axis.

Results and Discussion:

Treatment efficiency as a function of L-cysteine concentration (0-5 mM). A significant percentage of the TNFR:Fc protein in HIC Fraction #3 (average 10%) was converted to Fraction #2 when treatment was performed with 0.25 mM L-cysteine in the absence of L-cystine or EDTA in four replicate samples (FIG. 6). However, efficiency was greatly improved (from 45% to almost 70%) when treatment was performed at 1 mM L-cysteine or 5 mM L-cysteine (FIG. 6). The effect of cystine in these reaction conditions varied with EDTA presence (see below). For a given cell culture batch (samples from four different cell culture batches were treated), the treatment process was reproducible.

Treatment efficiency as a function of higher L-cysteine concentration (5-50 mM). Higher concentrations of L-cysteine (5, 15 and 50 mM L-cysteine) used to treat TNFR:Fc resulted in a decrease in HIC Fraction #3 from the starting material in each case, but 5 mM L-cysteine was most effective in promoting the accumulation of Fraction #2 (FIG. 7). It is estimated that higher concentrations of L-cysteine either significantly reduced the sulfhydryl moieties in the molecule or required too long to re-oxidize.

Treatment efficiency as a function of additional L-cysteine feeding. In order to attempt to increase disulfide exchange efficiency, TNFR:Fc was treated with 5 mM L-cysteine and incubated at 4 degrees Centigrade for 18 hours. Additional L-cysteine (0-5 mM) was then added, and the samples incubated at 4 degrees Centigrade for two additional days. Under these conditions, no significant effect on the ratio of HIC Fraction #3 to Fraction #2 was noted by additional L-cysteine feeding.

Effect of EDTA, cystine and L-cysteine. The effect of cystine (0-0.4 mM) in combination with L-cysteine (5 mM) on TNFR:Fc was assessed in the presence or absence of 1 mM EDTA. Optimal results in the presence of 1 mM EDTA occurred with concentrations of cystine in the range of 0.1-0.2 mM.

Figure 8A:
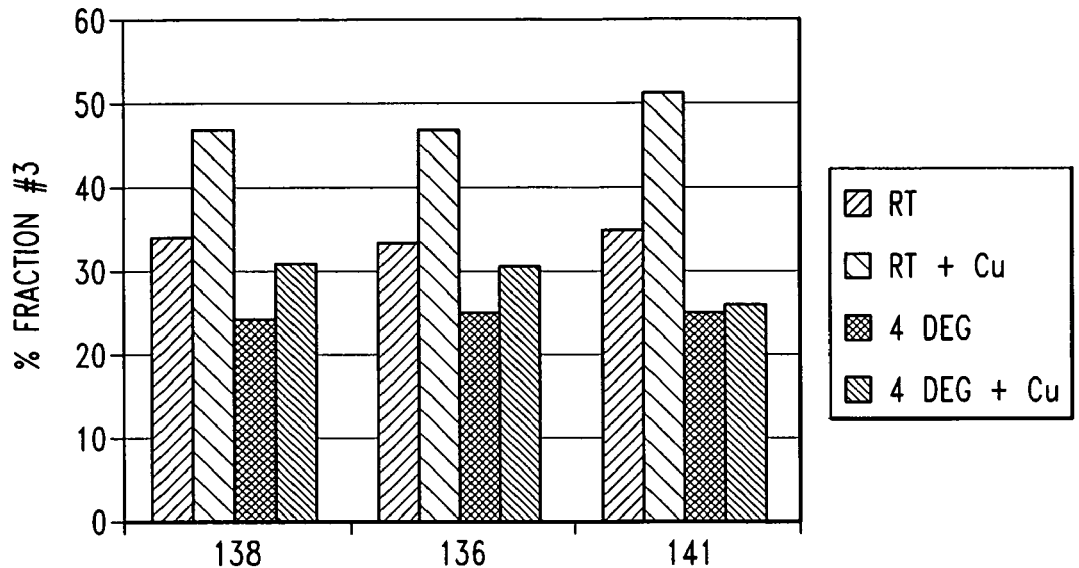
FIG. 8A presents changes in HIC Fraction #3 after 6 Hours.
Figure 8B:
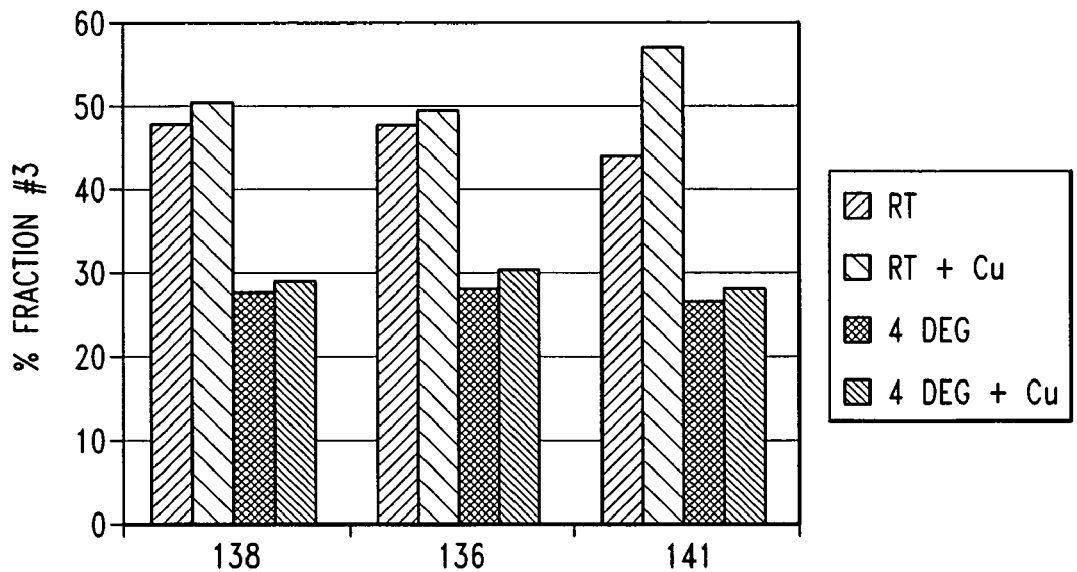
FIG. 8B presents changes in HIC Fraction #3 after 18 hours.

Copper, temperature and time effects. TNFR:Fc was treated at with 5 mM L-cysteine at 4 degrees and 22 degrees Centigrade for either 6 or 18 hours. Completion of treatment of TNFR:Fc was assayed by copper addition followed by HIC. After 6 hours of incubation, disulfide exchange is more complete at 4 degrees than 22 degrees, and treatment is clearly more complete after 18 hours at 4 degrees Centigrade (FIGS. 8A and 8B).

Comparison of analytical-versus preparative-scale L-cysteine treatment efficiency. Based upon the treatment conditions optimized at small scale, TNFR:Fc (2.5 mg/mL in 0.2 M Tris, pH 8.5) in either 3 mL or 20 L quantities were treated with 5 mM L-cysteine (in the absence of cystine or EDTA), incubated at 4 degrees Centigrade for 18 hours, diluted with and equal volume of 850 mM sodium citrate, 50 mM sodium phosphate, pH 6.5 to quench the treatment, and chromatographed on HIC. Control samples of Preparative and Analytical scale TNFR:Fc had 63% and 68% Fraction #3, respectively. After treatment with the above conditions, Fraction #3 was reduced to 28% in both Preparative and Analytical scales. Therefore the treatment efficiency was 56% and 59% for the Preparative and Analytical samples, respectively (Table 2). This experiment demonstrates that the process is amenable to larger scale treatment.

TABLE 2

Analytical vs. Preparative Scale Disulfide Exchange Procedure

|  | PREPARATIVE | | ANALYTICAL | |
| --- | --- | --- | --- | --- |
|  | Fraction #2 | Fraction #3 | Fraction #2 | Fraction #3 |
| Control | 37% | 63% | 32% | 68% |
| Exchange | 72% | 28% | 72% | 28% |
| Exchange "efficiency" |  | 56% |  | 59% |

Thus, although treatment redox efficiency is affected by free thiol concentration, temperature and time, it can be effectively optimized and performed over a wide range of variables. The treatment protocols can also be performed on both small and large scale with reproducibility.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method comprising:
contacting a preparation of a recombinant antibody that has been produced by mammalian cells with a reduction/oxidation coupling reagent, at a pH of about 7 to about 11, and isolating a fraction of the preparation of the recombinant antibody with a desired conformation, wherein the recombinant antibody with a desired conformation has a higher binding affinity than an undesired conformation for a cognate ligand of the antibody.

2. The method of claim 1 wherein the preparation of the recombinant antibody has been purified from a Protein A or Protein G column.

3. The method of claim 1 wherein the pH is from about 7 to about 10.

4. The method of claim 3 wherein the pH is about 7.6 to about 9.6.

5. The method of claim 4, wherein the pH is about 8.6.

6. The method of claim 1 wherein the reduction/oxidation coupling reagent comprises glutathione.

7. The method of claim 6 wherein the ratio of reduced glutathione to oxidized glutathione is about 1:1 to about 100:1.

8. The method of claim 1 wherein the reduction/oxidation coupling reagent comprises cysteine.

9. The method of claim 1 wherein the contacting step is performed for about 4 to about 16 hours.

10. The method of claim 1 wherein the contacting step is performed at about 25° C.

11. The method of claim 1 wherein the contacting step is performed at about 4° C.

12. The method of claim 1 wherein the contacting step is quenched by acidification.

13. The method of claim 1 wherein the isolating step comprises one or more chromatography steps.

14. The method of claim 1 wherein the antibody concentration is from about 0.5 to about 10 mg/ml.

15. The method of claim 1 wherein the ratio of reducing thiols in the reduction/oxidation coupling reagent to disulfide bonds in the protein is about 320:1 to about 64,000:1 (reducing thiols: disulfide bond).

16. The method of claim 1 further comprising formulating the fraction of the preparation of the recombinant antibody with the desired conformation in a sterile bulk form.

17. The method of claim 1 further comprising formulating the fraction of the preparation of the recombinant antibody with the desired conformation in a sterile unit dose form.

18. A method of promoting a desired conformation of a glycosylated recombinant antibody, the method comprising
contacting a preparation of the glycosylated recombinant antibody that contains a mixture of at least two configurational isomers of the glycosylated recombinant antibody with a reduction/oxidation coupling reagent for a time sufficient to increase the relative proportion of the desired configurational isomer and
determining the relative proportion of the desired configurational isomer in the mixture,
wherein the desired configurational isomer has a higher binding affinity than an undesired configurational isomer for a cognate ligand of the antibody.

19. The method of claim 18 wherein the preparation of the glycosylated recombinant antibody has been purified from a Protein A or Protein G column.

20. The method of claim 18 wherein the pH is from about 7 to about 10.

21. The method of claim 20 wherein the pH is about 8.6.

22. The method of claim 18 wherein the reduction/oxidation coupling reagent is selected from the group consisting of glutathione, cysteine, DTT (dithiothreitol), 2-mercaptoethanol and dithionitrobenzoate.

23. The method of claim 22 wherein the reduction/oxidation coupling reagent comprises reduced glutathione.

24. The method of claim 23 wherein the reduced glutathione is at a concentration of about 1 mM to about 10 mM.

25. The method of claim 22 wherein the reduction/oxidation coupling reagent comprises reduced cysteine.

26. The method of claim 22 wherein the ratio of reducing thiols in the reduction/oxidation coupling reagent to disulfide bonds in the protein is about 320:1 to about 64,000:1 (reducing thiols: disulfide bond).

27. The method of claim 18 wherein the antibody concentration is from about 0.5 to about 10 mg/ml.

28. The method of claim 18 wherein the contacting step is performed for about 4 to about 16 hours.

29. The method of claim 18 wherein the contacting step is performed at about 25° C.

30. The method of claim 18 wherein the contacting step is performed at about 4° C.

31. The method of claim 18 wherein the contacting step is quenched by acidification.

32. The method of claim 18 wherein the determining step comprises one or more chromatography steps.

33. The method of claim 18 wherein the determining step comprises a binding reaction.

34. The method of claim 18 comprising isolating a fraction of the preparation of the glycosylated recombinant antibody with the desired configurational isomer.

35. The method of claim 34 comprising formulating the desired configurational isomer in a sterile unit dose form.

* * * * *